United States Patent [19]

Harandi et al.

[11] Patent Number: 4,835,329

[45] Date of Patent: May 30, 1989

[54] PROCESS FOR PRODUCING HIGH OCTANE GASOLINE

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 130,258

[22] Filed: Dec. 8, 1987

[51] Int. Cl.$^4$ .............................................. C07C 41/06
[52] U.S. Cl. .................... 585/415; 585/407; 585/446; 568/697; 568/699
[58] Field of Search ............... 568/697, 699; 585/415, 585/331, 467, 533, 407, 408, 446

[56] References Cited

U.S. PATENT DOCUMENTS

| | | | |
|---|---|---|---|
| 3,760,024 | 9/1973 | Cattanach | 585/415 |
| 3,845,150 | 10/1974 | Yan et al. | 208/135 |
| 3,931,349 | 1/1976 | Kuo | 585/310 |
| 4,350,835 | 9/1982 | Chester et al. | 585/415 |
| 4,404,414 | 9/1983 | Penick et al. | 585/469 |
| 4,540,831 | 9/1985 | Briggs | 568/697 |
| 4,542,252 | 9/1985 | Graziani et al. | 585/640 |
| 4,544,776 | 10/1985 | Osterburg | 568/697 |
| 4,575,567 | 3/1986 | Vora | 568/697 |
| 4,684,757 | 8/1987 | Avidan | 585/331 |
| 4,746,761 | 5/1988 | Avidan | 585/331 |

OTHER PUBLICATIONS

U.S. Ser. No. 130,256, filed Dec. 8, 1987.
U.S. Ser. No. 130,258, filed Dec. 8, 1987.
U.S. Ser. No. 130,259, filed Dec. 8, 1987.
U.S. Ser. No. 130,260, filed Dec. 8, 1987.
U.S. Ser. No. 130,261, filed Dec. 8, 1987.

*Primary Examiner*—William R. Dixon, Jr.
*Assistant Examiner*—James M. Hunter, Jr.
*Attorney, Agent, or Firm*—Alexander J. McKillop; Charles J. Speciale; L. G. Wise

[57] ABSTRACT

An integrated process for the production of alkylate and etherate rich high octane gasoline streams comprising the etherification to produce MTBE and TAME in the presence of a high stoichiometric excess of methanol followed by the conversion of unreacted methanol in contact with zeolite-type catalyst in the presence of aromatics to produce alkylated aromatics in gasoline. The light paraffinic effluent from the methanol conversion zone is reacted in contact with zeolite catalyst under aromatization conditions to produce an aromatics feedstream for the methanol conversion reaction. A supplemental olefinic feedstream is provided to the methanol conversion zone after optionally serving as stripping medium for the separation of methanol and etherate-rich $C_5+$ gasoline from the etherification reaction.

17 Claims, 3 Drawing Sheets

PROCESS FOR PRODUCING HIGH OCTANE GASOLINE

This invention relates to a novel integrated process for the production of high octane gasoline. In particular, this invention relates to the conversion of $C_2+$ olefins and $C_3+$ paraffins to high octane gasoline in combination with the production of octane boosting methyl tertiary alkyl ethers and the conversion of methanol to gasoline and aromatics.

BACKGROUND OF THE INVENTION

The petroleum industry's ongoing quest for improved processes for the production of high octane gasoline, particularly high road octane gasoline, encompasses the search for processes that can extend the base of feedstocks convertible to high octane gasoline while providing high conversion yields in a safe and cost-effective operation. Since moving from lead additives as octane enhancers, the thrust of the industry's manufacturing program in high octane gasoline has moved increasingly toward the use of octane booster such as tertiary alkyl ethers, including methyl tertiary butyl ether (MTBE) and methyl tertiary amyl ether (TAME). Aromatics also continue as a major source of octane enhancers. As a consequence, much effort is directed toward the improvement of etherification processes for the production of MTBE and TAME and more cost-effective and safer processes for the production of aromatics.

Of the many technical challenges presented to research workers in the field in the effort to improve etherification processes for the production of MTBE and TAME, the management of unreacted methanol from the etherification step is one of the more difficult. Typically, to provide favorable equilibrium conditions, the reaction is carried out employing a slight stoichiometric excess of methanol where a large excess would be more effective. But the recovery and recycle of a large excess of unreacted methanol, dictated by both environmental and cost considerations, represents a substantial economic burden on the process as currently practiced.

Where the production of MTBE and TAME are relatively recent developments in the petroleum industry for the production of high octane gasoline, the production of aromatics for that purpose is a fixture of the industry. Acid catalyzed alkylation of aromatics is a commonplace and technologically mature process for the production of the octane enhancing components of gasoline. Substantial improvements to these well-studied processes by research workers in the field are hard to come by. Nevertheless, the challenge remains, for the changing status of feedstock availability, environmental constraints and cost reduction imperatives impose new requirements that must be met.

In comparatively recent years a new technology has emerged that provides surprising advantages in the conversion of oxygenates, olefins and paraffins to gasoline and aromatics. It has been found that medium pore size shape selective zeolite-type catalyst can be effectively employed to convert methanol to olefins and gasoline and convert olefins and paraffins to aromatics and alkylated aromatics. These processes are described in the following U.S. patents, all of which are incorporated herein in their entirety by reference: U.S. Pat. Nos. 3,931,349 to Tokuo, 4,404,414 to Penick et al., 4,150,062, 4,211,640 and 4,227,992 to Garwood et al., 3,960,978, 4,021,502 to Plank, Rosinski and Givens. Also, methanol conversion is described in the publication C. O. Chang, Catal. Rev. Sci. Eng., 25,1 (1983), also incorporated herein in its entirety.

It has been determined that the properties that these unique zeolite catalysts exhibit, and the processes developed through their implementation provide, a useful route to resolve many of the aforenoted problems associated with the production of methyl tertiary alkyl ethers, aromatics and alkylation of aromatics as currently employed in the industry to produce octane-enhancing components of gasoline.

Accordingly, it is an object of this invention to provide a new and highly useful integrated process for the production of high octane gasoline. Another object of the present invention is to provide an integrated process for the production of high octane gasoline incorporating etherification without methanol etherification feed recycle or recovery to produce MTBE and TAME.

Yet another object of the present invention is to provide an integrated process for the production of high octane gasoline that incorporates etherification in combination with the zeolite catalyzed conversion of methanol, olefins and paraffins.

Still another object of the present invention is to provide a process for the production of high octane gasoline by the zeolite catalyzed conversion of $C_2+$ olefins and $C_3+$ paraffins to aromatics and alkylated aromatics in combination with gasoline.

A further object of the present invention is to provide an integrated process for the production of high octane gasoline which can be readily combined with an unsaturated gas plant typically utilized in conjunction with a fluid catalytic cracking process.

SUMMARY OF THE INVENTION

A process has been discovered that accomplishes the aforestated objectives. The process substantially improves conventional etherification technology to produce MTBE and TAME and produces gasoline fractions rich in octane-enhancing ethers and alkylated aromatics. Most significantly, the conversion reaction to produce high octane gasoline utilizes $C_2+$ olefins and $C_3+$ paraffins as feedstock in a mixture with a stream comprising unreacted methanol from etherification. It has also been found that light paraffinic hydrocarbons from the conversion step can be aromatized and aromatic products therefrom fed to the zeolite conversion reactor where they undergo alkylation in the presence of olefins.

More specifically, the present invention comprises a process for the conversion of $C_2+$ olefins and $C_3+$ paraffins to high octane gasoline comprising the steps of:

(a) contacting a hydrocarbon feedstock mixture containing $C_4+$ iso-olefins and methanol with an etherification catalyst under etherification conditions whereby an etherification effluent stream is produced comprising methyl tertiary alkyl ethers, unreacted methanol and hydrocarbons;

(b) passing said effluent stream to a fractionator for separation in admixture with a hydrocarbon stripping medium to produce a liquid stream comprising methyl tertiary alkyl ether-rich $C_5+$ gasoline and a vapor stream comprising methanol and $C_5-$ hydrocarbons;

(c) reacting in admixture step b vapor stream and aromatic and olefins-rich hydrocarbon feedstock streams in contact with shape selective medium pore metallosilicate catalyst particles in a conversion zone at elevated temperature under olefins conversions and aromatics alkylation conditions to recover after separation reaction product streams comprising a first $C_5+$ gasoline stream rich in alkylated aromatics, a second $C_3$ and $C_4$ paraffinic hydrocarbon stream and a third $C_2-$ hydrocarbon stream;

(d) passing said second $C_3$ and $C_4$ paraffinic hydrocarbon stream to an aromatization zone in contacting with medium pore-size shape selective metallosilicate catalyst particles under paraffins aromatization conditions whereby an aromatization zone effluent stream comprising olefinic, aromatic and unreacted $C_3$ and $C_4$ paraffinic hydrocarbons is produced;

(e) separating said aromatization zone effluent stream and passing aromatic and olefinic components thereof to step C conversion zone whereby $C_5+$ gasoline rich in alkylated aromatics is produced.

It has been found that in the present invention a large stoichiometric excess of methanol is advantageously employed as feedstock to the etherification reactor, based on iso-olefins content in the hydrocarbon feedstock thereto. Further, it has been found that in the separation of the etherification effluent stream an ethylene-rich fuel gas is employed as stripping medium facilitating the separation of the methanol-hydrocarbon azeotropic mixture fed to the olefins conversion zone.

DETAILED DESCRIPTION OF THE INVENTION

In the preferred embodiment of the instant invention the principle components of known processes are integrated in a manner providing a highly advantageous and surprising advancement in refinery technology leading to the production of high octane gasoline. Known processes are combined in a unique configuration that provides enhancement of the performance of component processes as well as achieving surprising advantages for the integrated process. The processes integrated include etherification to produce MTBE and TAME, the conversion of methanol to olefin and gasoline over a zeolite-type catalyst and the conversion of light paraffinic hydrocarbons to aromatics, known as the M-2 Forming process. In subsequent sections each of the prior processes will be described. However, in FIG. 1, the fully integrated process of the present invention incorporating these individual processes is presented in a schematic drawing.

Figure 1:
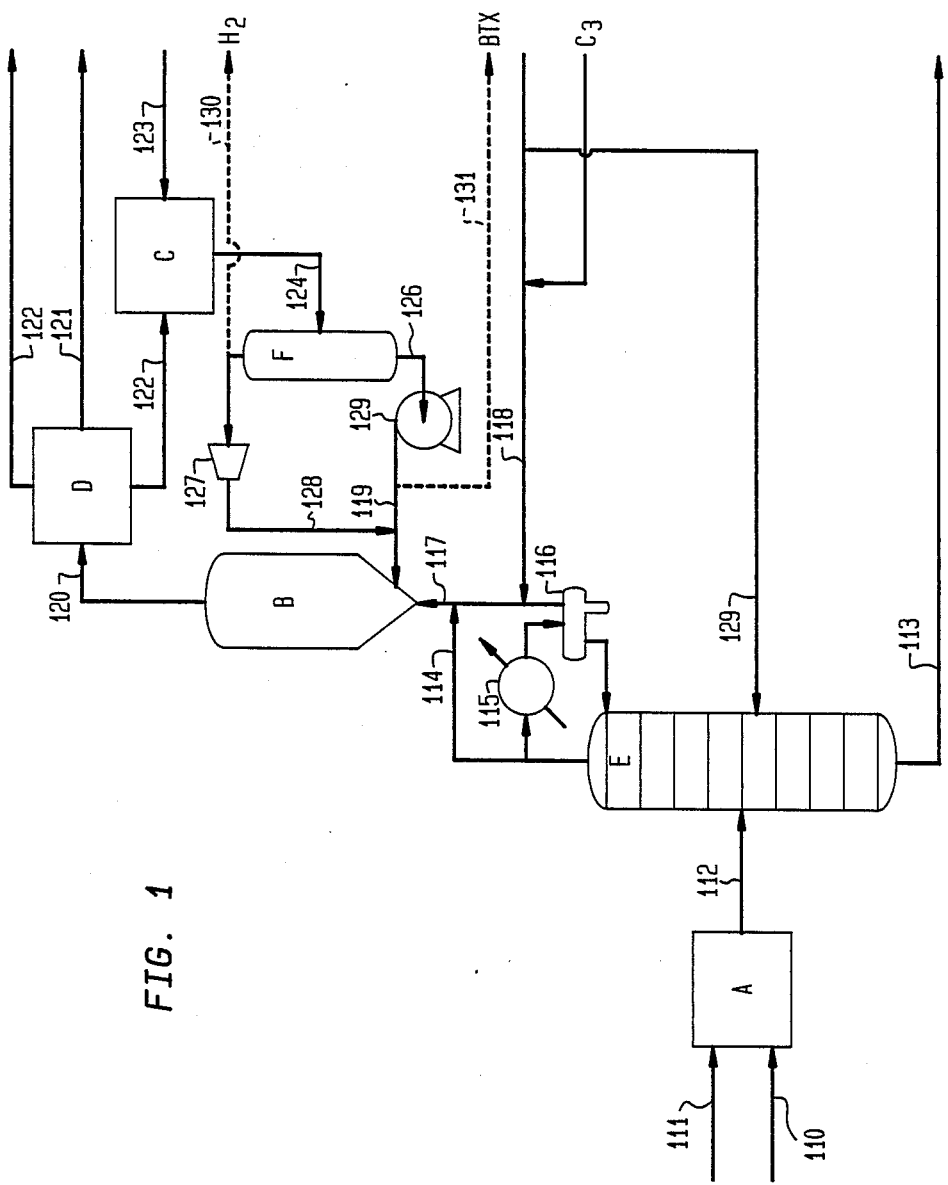
FIG. 1 is a schematic drawing of the process flow diagram of the instant invention.

Referring now to FIG. 1, the present invention involves the integration of etherification reaction unit A with methanol to olefins and gasoline reaction unit B and aromatization unit, or M2 Forming, reactor unit C. These are combined through etherification separation unit E, the methanol and olefins to gasoline separation and recovery unit D and the aromatization separation unit F. The reaction conditions in etherification, methanol and olefins conversion to gasoline, and in the aromatization process are essentially those encompassing the range of conditions under which these known processes are conventionally conducted as described hereinafter.

In FIG. 1, the feedstream to the etherification reaction section comprise crude or pure methanol and a hydrocarbon stream rich in $C_4+$ iso-olefins, in particularly, isobutene and isoamylene. Methanol is passed 110 to the etherification reaction unit generally in an amount representing a large stoichiometric excess over iso-olefins passed 111 to etherification reactor in the hydrocarbon feedstream. An important feature of the present invention is that the amount of excess methanol is much higher than the amount of excess methanol fed to etherification reactors as practiced in prior art heretofore. Accordingly, the equilibrium dependent etherification reaction is driven toward the formation of ethers. However, the unique downstream integration of methanol to gasoline reactor unit B readily accommodates and converts excess methanol, obviating separation and recycle of methanol as typically practiced in etherification processes to produce methyl tertiary butyl ether and methyl tertiary amyl ether. Following etherification the product is passed 112 to a fractionator and separated into a bottom effluent stream 113 comprising an ether-rich stream of $C_5+$ gasoline. The fractionator overhead stream comprises unreacted methanol, $C_4-$ and some $C_5$ hydrocarbons. To enhance the separation of methanol in separator E a stripping gas is passed to the separator. The stripping gas may be hydrogen or nitrogen or a hydrocarbon gas stream but preferably a hydrocarbon gas stream rich in ethylene. It is well known that the separation of methanol is complicated by the formation of a methanol-hydrocarbon azeotrope generally containing about 2 to 3% methanol. While the addition of a stripping gas to the separation process in E is an optional consideration, the added hydrocarbon gas can substantially contribute to the more complete separation of methanol. A portion of the overhead stream 114 is recycled to separator E as a liquid reflux stream after cooling 115 and liquid-vapor separation 116. The vapor fraction from separator 116 is passed to the MTG reactor in combination with the unrecycled portion of stream 114 and olefins-rich hydrocarbon feedstream 118 to reactor B. An aromatic stream 119 and/or an olefinic stream 128 is also fed to the MTG reactor from the M2 Forming reactor separator F.

In reactor B, under MTG reaction conditions, methanol is converted to olefins and olefins are converted to gasoline. Also, under the same conversion conditions, an alkylation reaction occurs between methanol and other reactants and between olefins and aromatics whereby alkylated aromatics are produced. The foregoing reactions all proceed in contact with medium-pore size shape selective metallosilicate catalyst, such as zeolite-type catalyst. Preferably, the zeolite-type catalyst is an aluminosilicate zeolite-type catalyst, such as ZSM-5. The MTG reaction product is passed 120 to a separation and recovery section D where a $C_5+$ gasoline stream 121 rich in aromatics is separated as well as a fuel gas stream 122 comprising $C_2-$ hydrocarbons and rich in hydrogen.

From the separation and recovery section D a $C_3$ and $C_4$ stream is also separated comprising primarily paraffinic hydrocarbons. The paraffinic hydrocarbon stream is passed to M-2 Forming aromatization reactor C for conversion to aromatics at relatively low pressure and high temperature. Optionally, the paraffinic feedstream 122 may be supplemented by fresh paraffinic feed 123. The aromatization effluent stream 124 after cooling, is separated in separator F to a vapor overhead 125 and a liquid bottom fraction 126. In compressor 127 the vapor fraction pressure is raised and passed 128 to reactor B. Through pump 129, the liquid bottom fraction is passed to reactor B. Both liquid and vapor fractions from separator F comprise primarily olefinic and aromatic hydrocarbons, respectively. Alternatively the M-2 Former reactor may be operated such that a negligible amount of olefins are produced. In this case, the M-2 Forming vapor product can be separated as $H_2$ rich gas 130. The M-2 Forming aromatic gasoline may be directly sent to the gasoline pool or sold as BTX 131.

Etherification

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The reaction of methanol with isobutylene and isoamylenes at moderate conditions with a resin catalyst is known technology, as provided by R. W. Reynolds, et al., The *Oil and Gas Journal,* June 16, 1975, and S. Pecci and T. Floris, *Hydrocarbon Processing,* December 1977. An article entitled "MTBE and TAME—A Good Octane Boosting Combo," by J. D. Chase, et al., *The Oil and Gas Journal,* Apr. 9, 1979, pages 149–152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J. D. Chase, et al., *Oil and Gas Journal,* Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$–$C_7$ iso-olefins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

Methanol and Olefins to Gasoline

In the integrated process of the present invention, zeolite type catalyst converts alcohol, such as methanol, and olefins to gasoline and other liquid products. It is well-known that the conversion of methanol to gasoline proceeds through the formation of ethers and olefins which, in turn, oligomerize to higher hydrocarbon gasoline and distillate products. In the process for catalytic conversion of olefins to heavier hydrocarbons by oligomerization using acid crystalline zeolite, such as ZSM-5 type catalyst, process conditions can be varied to favor the formation of either gasoline or distillate range products. In the present invention, the feed to the conversion reactor is preferably a combined feed of methanol and olefins. Operating details for the typical conversion of olefins to gasoline or distillate are disclosed in U.S. Pat. Nos. 4,456,779; 4,497,968 to Owen et al. and 4,433,185 to Tabak, which are incorporated herein by reference.

A conventional methanol to gasoline (MTG) plant design may be readily adapted to process the combined methanol or methanol and olefins feed of the instant invention.

Figure 2:
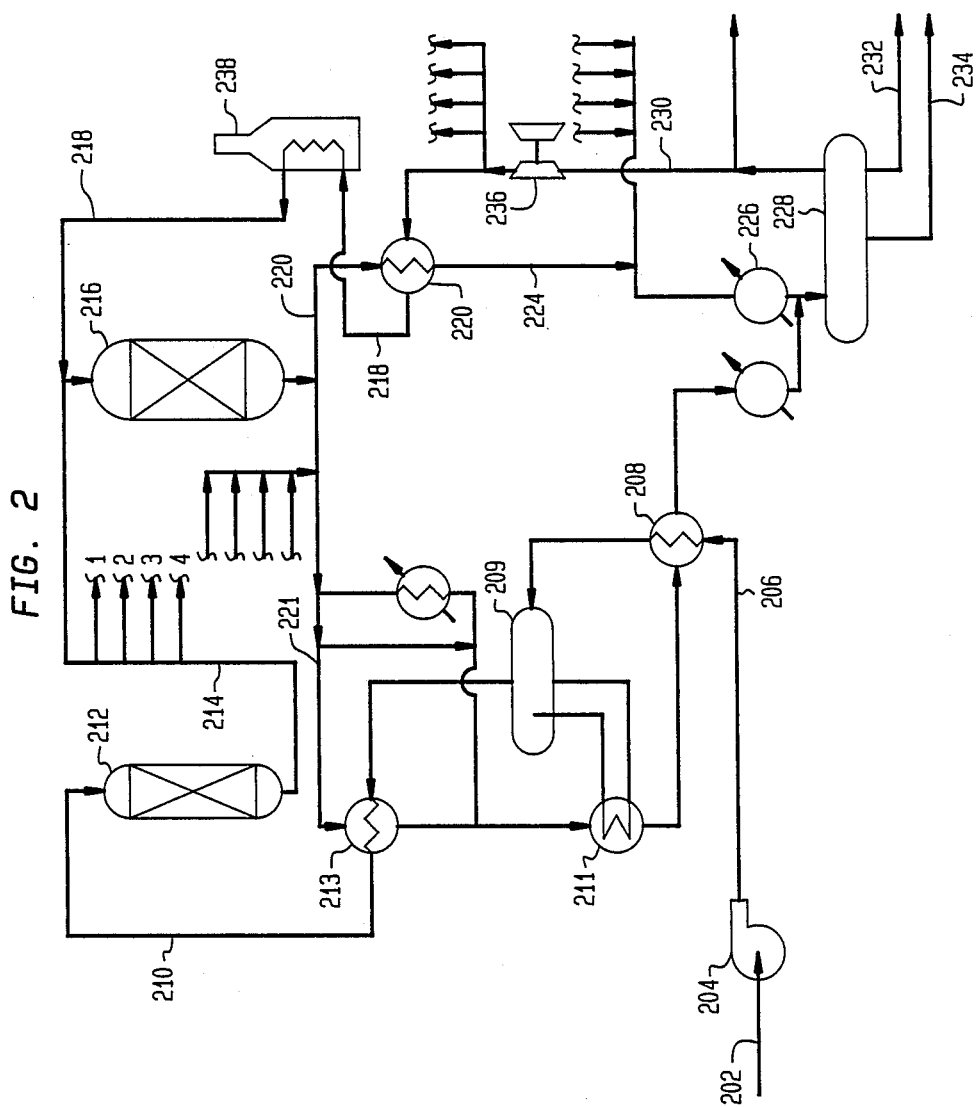
FIG. 2 is a flow diagram of the process for the conversion of methanol to gasoline known as MTG.

Referring now to FIG. 2, a typical process flow diagram of the MTG process is presented. Crude methanol in a liquid phase condition is charged to the process by conduit 202 communicating with pump 204. The methanol is compressed to about 160 psig in pump 204 and then passed by conduit 206 to heat exchanger 8 wherein the temperature of the liquid methanol is raised to about 400 degrees F. The thus preheated methanol is vaporized in indirect heat exchanger 208 before it is passed by conduit 210 to the inlet of the dimethyl ether forming catalytic reactor 212. In catalyst containing reactor 212, a fixed bed of gamma alumina catalyst is maintained as a fixed bed of catalyst through which the methanol reactant passed downwardly through or as an annular bed of catalyst for radial flow of reactant material therethrough. A single down-flow fixed catalyst bed or a plurality of separate fixed downflow catalyst bed are arranged for converting the methanol feed under restricted temperature conditions as herein described to essentially an equilibrium product comprising methanol, dimethyl ether or water existing at a temperature of about 315 C. (600 F.). due to the exothermic temperature rise catalytically generated in the operation. The equilibrium product thus obtained may be construed as an ether rich product which is then passed by conduit 214 to a second reactor stage 216 housing one or more separate and sequentially arranged beds of a ZSM-5 type of crystalline zeolite. For the purpose of this specific discussion, the crystalline zeolite employed in the second reactor stage is a HZSM-5 crystalline zeolite.

In the combination operation herein described, it is preferred to employ a low pressure drop catalyst system in reactor 216. A diluent material introduced by conduit 218 is combined with the ether rich effluent obtained as hereinbefore discussed before contact of the mixture is made with the HZSM-5 crystalline zeolite catalyst under heat generating or exothermic reaction conditions controlled to restrict the temperature increase between the reactor inlet and reactor outlet not to exceed about (95 C.). and preferably not to exceed about 150 C. The conversion of the ether rich effluent by the HZSM-5 catalyst is highly exothermic as discussed above and controlled within desired limits by use of gasiform heat dissipating diluent material. During this highly exothermic operation the ether rich effluent or equilibrium mixture comprising dimethyl ether, methanol and water is controlled to effect the conversion thereof to gasoline boiling range components comprising aromatic and isoparaffins. The aromatic components comprising benzene, toluene and xylene are preferred components over the higher boiling durene aromatic material and every effort is made through temperature restraint, reactant partial pressure, space velocity and reactant plug flow operation to promote this end.

The product effluent of the HZSM-5 reaction zone 216 is passed through one or more cooling steps to reduce the temperature to a desired low temperature. In the specific arrangement of the figure, the effluent is passed by conduit 220 to heat exchanger 222 wherein the effluent temperature is reduced to about 470 degrees F. by indirect heat exchange with diluent material removed therefrom by conduit 218. The diluent will be at a temperature of about 600 degrees F. The partially cooled effluent is removed from heat exchanger 222 and passed by conduit 224 to heat exchanger 226 wherein a further cooling of the effluent to about 440 degrees F. is accomplished.

A portion of reactor 216 effluent is passed through conduit 221 through heat exchangers 208, 211 and 213 to preheat methanol. The effluent is combined in separator 228 after temperature reduction from about 425 C. (800 F.) to 37 C. (100 F.). Recycled gas is separated by conduit 230 and product gasoline is separated by conduit 232 and waste water by conduit 234. Recycle gas, after compression in compressors 236 is returned to the reactor as diluent after heating in heater 238. Diluent temperature is raised from about 37 C. (100 F.) to about 315 C. (600 F.), although recycle gas can be between 293 C. to 398 C. (560 F. to 750 F.), but preferably about 310 C. to 371 C. (590 to 700 F.). Inlet temperatures to the first reactor are normally about 298 C. to 398 C. (570 F. to 750 F.) but preferably about 329 C. to 371 C. (625 F. to 700 F.), although in certain processes temperatures as low as 276 C. (530 F.) may be desirable.

M-2 Forming (Aromatization)

Figure 3:
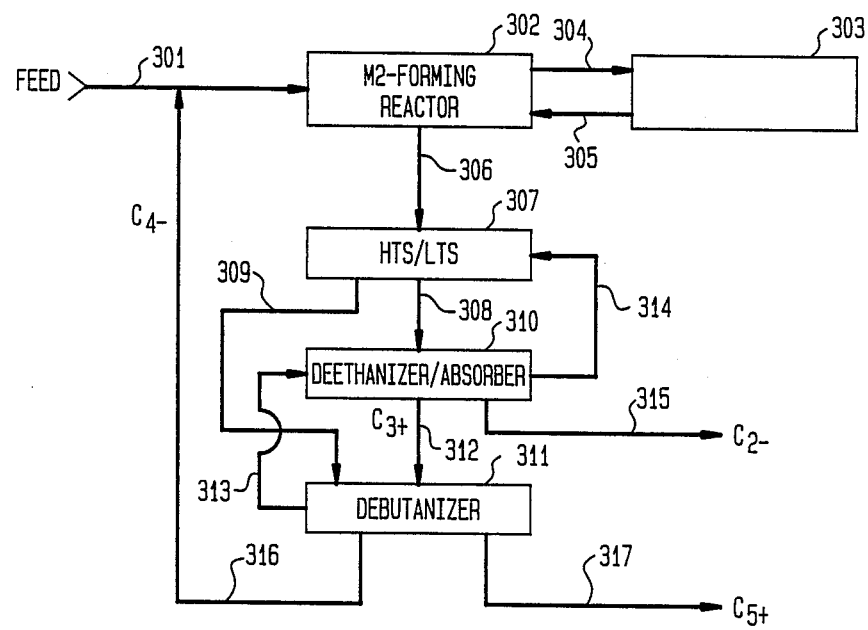
FIG. 3 is a schematic drawing of the process for the conversion of light hydrocarbons to aromatics (M-2 Forming).

Referring to FIG. 3, a schematic flow diagram of the modified M2 Forming Aromatization process is shown. Typically, an essentially paraffinic or mixed paraffinic olefinic feed 301 is passed to an M2 Forming reactor vessel 302 containing ZSM-5 catalyst. A catalyst regenerator vessel 3 is connected therewith (304, 305) for recycling and regenerating ZSM-5 catalyst, and adding fresh catalyst 318 as appropriate. The light aliphatic, paraffinic/olefinic feed is converted under conditions described in U.S. Pat. No. 3,760,024 to Cattanach, incorporated herein by reference. The operating conditions are temperatures from 300 to 750 C. and pressures from atmospheric to 3600 KPa (500 psig), preferably about 500 degrees C. and 350 kPa. The reaction products comprise an effluent stream of light gases such as hydrogen and methane unconverted light hydrocarbons and $C_5+$ aromatics. After cooling the effluent stream the products are passed 306 to high temperature and low temperature product separators 307 where a low temperature product fraction 308 is passed to a light gas and $C_2$ absorber/deethanizer system 310 while a high temperature fraction is passed 309 to a debutanizer 311 in addition to a $C_3+$ fraction 312 from the deethanizer. A recycle stream 314 is taken from the deethanizer/absorber system along with a $C_2-$ product stream 315. In addition to recycle stream 313, the debutanizer provides the aromatics $C_5+$ product stream 317 and an unconverted $C_4-$ hydrocarbon stream 316 which is recycled to extinction to the light hydrocarbon feedstream 301.

Catalyst

The conversion of methanol, methanol equivalent, olefins and paraffins to gasoline, alkylated aromatics, and aromatics occurs under a broad range of operating conditions, but is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica: alumina ratio is correctly determined.

Preferred zeolites which have the specified values of Constraint Index and silica:alumina ratio include zeolites ZSM-5, ZSM-11, ZSM-12, ZSM-35, ZSM-38 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), 4,046,859 (ZSM-38) and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500 degrees C. for 1 hour or more. The hydrogen form can then be obtained by base exchange with ammonium salts followed by calcination e.g. at 500 degrees C. in air. Other cations, e.g. metal cations, such as Ga, Zn, Cu, Pt and Fe, can be introduced by conventional base exchange techniques.

The significant advantages of the present invention are shown in Table 1, where Column A is the hydrocarbon feed, Column B is product distribution for a conventional etherification process and Column C is the product distribution for the process of the present invention. As shown in Table 1, the proposed process makes 159.5 Mlb/hr of $C_5+$ high octane gasoline based on 186 Mlb/hr $C_5-$ FCC feed rate. The corresponding conventional etherification $C_5+$ gasoline make is 76.21 Mlb/hr.

TABLE 1
ETHERIFICATION PRODUCT DISTRIBUTION
(BASED ON CORYTON 55 TBD FCC
MAXIMUM GASOLINE OPERATIONS)

| MLB/HR | A | B* | C** |
|---|---|---|---|
| $C_1$ & (inerts) | 11.40 | 11.40 | 19.67 |
| $C_2^=$ | 6.80 | 6.80 | 0.54 |
| $C_2$ | 12.00 | 12.00 | 17.91 |
| $C_3^=$ | 25.78 | 25.78 | 0.57 |
| $C_3$ | 8.97 | 8.97 | 3.57 |
| $iC_4$ | 18.81 | 18.81 | 1.59 |
| $nC_4^=$ | 33.43 | 33.43 | 0.62 |
| $nC_4$ | 5.91 | 5.91 | 0.56 |
| $iC_4^=$ | 15.89 | 1.11 | 0.01 |
| $nC_5^=$ | 13.53 | 13.53 | 5.39 |
| $iC_5$ | 10.70 | 10.70 | 10.69 |
| $nC_5$ | 2.79 | 2.79 | 2.79 |
| $iC_5^=$ | 20.03 | 7.01 | 2.39 |
| Benzene | — | — | 9.35 |
| Toluene | — | — | 19.48 |
| xylene | — | — | 7.74 |
| $C_9+$ Aromatics | — | — | 2.32 |
| MOG $C_5+$ | — | — | 54.71 |
| MTBE | — | 23.21 | 24.21 |
| TAME | — | 18.97 | 20.43 |
| $H_2O$ | 0.08 | — | 4.25 |
| Total | 186.12 | 200.42 | 208.79 |

*Corresponds to 14.7 MLB/HR Total Methanol Feed Rate.
**Corresponds to 22.77 MLB/HR Total Methanol Feed Rate.

While the invention has been described by specific embodiments, there is no attempt to limit the inventive concept except as set forth in the following claims.

What is claimed is:

1. A process for conversion of $C_2+$ olefins and $C_3+$ paraffins to high octane $C_5+$ gasoline rich in methyl tertiary alkyl either and $C_5+$ gasoline rich in alkylated aromatics comprising the steps of:
    (a) contacting a hydrocarbon feedstock mixture containing $C_4+$ iso-olefins and methanol with an etherification catalyst under etherification conditions whereby an etherification effluent stream is produced comprising methyl tertiary alkyl ethers, unreacted methanol and hydrocarbons;
    (b) passing said effluent stream to a fractionator for separation in contact with a hydrocarbon stripping medium to produce a liquid stream comprising $C_5+$ gasoline rich in methyl tertiary alkyl ether and a vapor stream comprising methanol and $C_5$ and lower hydrocarbons;
    (c) reacting step b vapor stream and a feedstock stream comprising aromatic and olefins-rich hydrocarbons in contact with shape-selective medium pore metallosilicate catalyst particles in a conversion zone at elevated temperature under olefins conversion and aromatics alkylation conditions to recover after separation reaction product streams comprising a first $C_5+$ gasoline stream rich in alkylated aromatics, a second stream comprising $C_3$ and $C_4$ paraffinic hydrocarbons and a third stream comprising $C_2$ and lower hydrocarbons;
    (d) passing said second $C_3$ and $C_4$ paraffinic hydrocarbon stream to an aromatization zone and contacting with medium-pore size shape selective metallosilicate catalyst particles under paraffins aromatization conditions whereby an aromatization zone effluent stream comprising olefinic, aromatic and unreacted $C_3$ and $C_4$ paraffinic hydrocarbons is produced; and
    (e) separating said aromatization zone effluent stream and passing aromatic and olefinic components thereof to step c conversion zone whereby $C_5+$ gasoline rich in alkylated aromatics is produced.

2. The process of claim 1 comprising the further step of recycling step d unreacted $C_3$ and $C_4$ paraffinic hydrocarbons to extinction whereby the yield of gasoline is increased.

3. The process of claim 1 wherein step d aromatization zone comprises movable bed, fixed bed, tubular bed or fluid bed catalytic reactors.

4. The process of claim 3 wherein said aromatization conditions comprise low pressure between 50 and 1000 kPa and temperature between 530 to 800 C. and WHSV between 0.1 and 500.

5. The process of claim 3 wherein said metallosilicate catalyst particles comprise zeolite aluminosilicate, gallium-containing aluminosilicate or gallium-silicate catalyst particles.

6. The process of claim 1 wherein step d separation of aromatization zone effluent stream comprises the steps of cooling said effluent stream; fractionating said effluent stream to provide a vapor overhead stream and liquid bottom stream, wherein said streams are passed to step d conversion zone by compressing of the vapor stream and pumping of the liquid stream.

7. The process of claim 1 wherein the etherification conditions comprise between 1 and 200 weight percent stoichiometric excess of methanol based on iso-olefins in the hydrocarbon feedstock.

8. The process of claim 7 wherein the stoichiometric excess of methanol is about 30 wt.

9. The process of claim 1 wherein step b hydrocarbon stripping medium comprises ethylene-rich fuel gas or olefin rich $C_3$ stream.

10. The process of claim 1 wherein step c conversion conditions comprise pressure between 50 and 3000 kPa and temperature between 250 and 530 C.

11. The process of claim 10 wherein pressure is about 1300 kPa and temperature is about 427 C.

12. The process of claim 1 wherein step c metallosilicate catalyst particles comprise zeolite aluminosilicate.

13. The process of claim 12 wherein said zeolite aluminosilicate comprises ZSM-5.

14. The process of claim 1 wherein step c olefins-rich hydrocarbon feedstock stream comprises ethylene and propene rich $C_2$-$C_6$ hydrocarbon stream.

15. The process of claim 1 wherein step b ether-rich $C_5+$ gasoline comprises $C_5+$ gasoline rich in methyl tertiary butyl ether and methyl tertiary amyl ether.

16. The process of claim 1 wherein step a hydrocarbon feedstock mixtures comprise feedstock rich in isobutene and isoamylene whereby methyl tertiary butyl ether and methyl tertiary amyl ether is produced.

17. The process of claim 1 wherein step (c) second stream after separation contains $C_2+$ paraffins; passing said second stream to step (d) aromatization zone whereby $C_2+$ paraffins are converted to aromatics and olefins.

* * * * *